(12) United States Patent
Rideout et al.

(10) Patent No.: US 6,436,933 B1
(45) Date of Patent: Aug. 20, 2002

(54) INHIBITORS OF ANTHRAX LETHAL FACTOR ACTIVITY

(75) Inventors: Darryl Rideout; Venkatachalapathi V. Yalamoori; Kalyanaraman Ramnarayan; Mark Shenderovich; Jian Hua Zheng; Jason Sun; Christina Niemeyer, all of San Diego, CA (US)

(73) Assignee: Structural Bioinformatics Inc., San Diego, CA (US)

( * ) Notice: Subject to any disclaimer, the term of this patent is extended or adjusted under 35 U.S.C. 154(b) by 0 days.

(21) Appl. No.: 09/818,259

(22) Filed: Mar. 26, 2001

(51) Int. Cl.[7] .............................................. A61K 31/535
(52) U.S. Cl. ............................... 514/235.8; 514/235.8; 514/235.2; 514/234.5; 514/235.5; 514/238.5
(58) Field of Search ........................... 514/235.2, 234.5, 514/235.5, 238.5, 235.8

(56) References Cited

U.S. PATENT DOCUMENTS 4,877,875 A * 10/1989 Yaso et al. .................. 544/116

* cited by examiner

Primary Examiner—Shep K. Rose
Assistant Examiner—Donna Jagoe
(74) Attorney, Agent, or Firm—James C. Weseman, Esq.; The Law Offies of James C. Weseman

(57) ABSTRACT

Methods and compositions that act as specific inhibitors of ALF activity for the prophylaxis and treatment of anthrax infections.

3 Claims, 2 Drawing Sheets

| EXAMPLE # | molstructure |
|---|---|
| 1 |  |
| 3 |  |
| 4 |  |
| 2 |  |
| 5 |  |
| 6 |  |
| 7 |  |
| 8 |  |
| 9 |  |
| 10 |  |

| EXAMPLE # | molstructure |
|---|---|
| 11 |  |
| 12 |  |
| 13 |  |
| 14 |  |
| 15 |  |
| 16 |  |
| 17 |  |
| 18 |  |
| 19 |  |
| 20 |  |
| 21 |  |

| EXAMPLE # | molstructure | EXAMPLE # | molstructure |
|---|---|---|---|
| 22 |  | 32 |  |
| 23 |  | 33 |  |
| 24 |  | 34 |  |
| 25 |  | 35 |  |
| 26 |  | 36 |  |
| 27 |  | 37 |  |
| 28 |  | 38 |  |
| 29 |  | 39 |  |
| 30 |  | 40 |  |
| 31 |  | | |

INHIBITORS OF ANTHRAX LETHAL FACTOR ACTIVITY

GOVERNMENT SUPPORT

This invention was made with the support of the United States Government and the United States Government has certain rights in the invention.

TECHNICAL FIELD

The present invention relates to the prophylaxis and treatment of anthrax infections and, more particularly, to compounds that act as specific inhibitors of Anthrax Lethal Factor activity, methods and means for making such inhibitors and their use as pharmaceuticals.

BACKGROUND OF THE INVENTION

Anthrax is a zoonotic illness recognized since antiquity. In the 1870s, Robert Koch demonstrated for the first time the bacterial origin of a specific disease, with his studies on experimental anthrax, and also discovered the spore stage that allows persistence of the organism in the environment. Shortly afterward, *Bacillus anthracis* was recognized as the cause of woolsorter disease (inhalational anthrax). William Greenfield's successful immunization of livestock against anthrax soon followed in 1880, although Louis Pasteur's 1881 trial of a heat-cured anthrax vaccine in sheep is usually remembered as the initial use of a live vaccine.

Human cases of anthrax are invariably zoonotic in origin, with no convincing data to suggest that human-to-human transmission has ever taken place. Primary disease takes one of three forms: (1) Cutaneous, the most common, results from contact with an infected animal or animal products; (2) Inhalational is much less common and a result of spore deposition in the lungs, while (3) Gastrointestinal is due to ingestion of infected meat. Most literature cites cutaneous disease as constituting the large majority (up to 95%) of cases.

*Bacillus anthracis* is a large, gram-positive, sporulating rod, with square or concave ends. Growing readily on sheep blood agar, *B. anthracis* forms rough, gray-white colonies of four to five mm, with characteristic comma-shaped or "comet-tail" protrusions. Several tests are helpful in differentiating *B. anthracis* from other Bacillus species. *Bacillus anthracis* is characterized by an absence of the following: Hemolysis, motility, growth on phenylethyl alcohol blood agar, gelatin hydrolysis, and salicin fermentation. *Bacillus anthracis* may also be identified by the API-20E and API-50CHB systems used in conjunction with the previously mentioned biochemical tests. Definitive identification is based on immunological demonstration of the production of protein toxin components and the poly-D-glutamic acid capsule, susceptibility to a specific bacteriophage, and virulence for mice and guinea pigs. The virulence of *B anthracis* is dependent on two toxins, lethal toxin and edema toxin, as well as on the bacterial capsule. The importance of a toxin in pathogenesis was demonstrated in the early 1950s, when sterile plasma from anthrax-infected guinea pigs caused disease when injected into other animals (Smith, H. and J. Keppie, *Nature* 173:869–870 (1954)). It has since been shown that the anthrax toxins are composed of three entities, which in concert lead to some of the clinical effects of anthrax (Stanley, J. L. and H. Smith, *J. Gen Microbiol* 26:49–66 (1961); Beall, F. A. et al., *J. Bacteriol* 83:1274–1280 (1962)). The first of these, protective antigen, is an 83 kd protein so named because it is the main protective constituent of anthrax vaccines. The protective antigen binds to target cell receptors and is then proteolytically cleaved of a 20 kd fragment. A second binding domain is then exposed on the 63 kd remnant, which combines with either edema factor, an 89 kd protein, to form edema toxin, or lethal factor, a 90 kd protein, to form lethal toxin (Leppla, S. H. et al., *Salisbury Med Bull Suppl.*, 68:41–43 (1990)). The respective toxins are then transported across the cell membrane, and the factors are released into the cytosol where they exert their effects. Edema factor, a calmodulin-dependent adenylate cyclase, acts by converting adenosine triphosphate to cyclic adenosine monophosphate. Intracellular cyclic adenosine monophosphate levels are thereby increased, leading to the edema characteristic of the disease (Leppla, S. H., *Proc Natl Acad Sci USA* 79:3162–3166 (1982)). The action of lethal factor, believed to be a metalloprotease, is less well understood. Lethal toxin has been demonstrated to lyse macrophages at high concentration, while inducing the release of tumor necrosis factor and interleukin 1 at lower concentrations (Hanna, P. C. et al., *Proc Natl Acad Sci USA* 90:10198–10201 (1993); Freidlander, A. M., *J Biol Chem.* 261:7123–7126 (1986)).

It has been shown that a combination of antibodies to interleukin 1 and tumor necrosis factor was protective against a lethal challenge of anthrax toxin in mice, as was the human interleukin 1 receptor antagonist (Hanna, P. C. et al., *Proc Natl Acad Sci USA* 90:10198–10201 (1993)). Macrophage-depleted mice were shown to resist lethal toxin challenge, but to succumb when macrophages were reconstituted. The genes for both the toxin and the capsule are carried by plasmids, designated pX01[33] and pX02, respectively (Green, B. D. et al., *Bacillus anthracis Infect Immunol.* 49:291–297 (1985); Uchida, I. Et al., *J Gen Microbiol.* 131:363–367 (1985)).

Disease occurs when spores enter the body, germinate to the bacillary form, and multiply. In cutaneous disease, spores gain entry through cuts, abrasions, or in some cases through certain species of biting flies. Germination is thought to take place in macrophages, and toxin release results in edema and tissue necrosis but little or no purulence, probably because of inhibitory effects of the toxins on leukocytes. Generally, cutaneous disease remains localized, although if untreated it may become systemic in up to 20% of cases, with dissemination via the lymphatics. In the gastrointestinal form, *B. anthracis* is ingested in spore-contaminated meat, and may invade anywhere in the gastrointestinal tract. Transport to mesenteric or other regional lymph nodes and replication occur, resulting in dissemination, bacteremia, and a high mortality rate. As in other forms of anthrax, involved nodes show an impressive degree of hemorrhage and necrosis.

The pathogenesis of inhalational anthrax is more fully studied and understood. Inhaled spores are ingested by pulmonary macrophages and carried to hilar and mediastinal lymph nodes, where they germinate and multiply, elaborating toxins and overwhelming the clearance ability of the regional nodes. Bacteremia occurs, and death soon follows. Penicillin remains the drug of choice for treatment of susceptible strains of anthrax, with ciprofloxacin and doxycycline employed as suitable alternatives. Some data in experimental models of infection suggest that the addition of streptomycin to penicillin may also be helpful. Penicillin resistance remains extremely rare in naturally occurring strains; however, the possibility of resistance should be suspected in a biological warfare attack. Cutaneous anthrax may be treated orally, while gastrointestinal or inhalational disease ordinarily should receive high doses of intravenous antibiotics (penicillin G, 4 million units every 4 hours; ciprofloxacin, 400 mg every 12 hours; or doxycycline hyclate, 100 mg every 12 hours). The more severe forms require intensive supportive care and have a high mortality rate despite optimal therapy. The use of anti-anthrax serum, while no longer available for human use except in the former Soviet Union, was thought to be of some use in the preantibiotic era, although no controlled studies were performed.

Although anthrax vaccination dates to the early studies of Greenfield and Pasteur, the "modern" era of anthrax vaccine development began with a toxin-producing, unencapsulated (attenuated) strain in the 1930s. Administered to livestock as a single dose with a yearly booster, the vaccine was highly immunogenic and well tolerated in most species, although somewhat virulent in goats and llamas. This preparation is essentially the same as that administered to livestock around the world today. The first human vaccine was developed in the 1940s from nonencapsulated strains. This live spore vaccine, similar to Sterne's product, is administered by scarification with a yearly booster. Studies show a reduced risk of 5- to 15-fold in occupationally exposed workers (Shlyakhov, E. N and E. Rubenstein, Vaccine 12:727–730 (1994)).

British and U.S. vaccines were developed in the 1950s and early 1960s, with the U.S. product an aluminum hydroxide-adsorbed, cell-free culture filtrate of an unencapsulated strain (V770-NP1-R), and the British vaccine an alum-precipitated, cell-free filtrate of a Sterne strain culture. The U.S. vaccine has been shown to induce high levels of antibody only to protective antigen, while the British vaccine induces lower levels of antibody to protective antigen but measurable antibodies against lethal factor and edema factor (Turnbull, P. C. B. et al., Infect Immunol. 52:356–363 (1986); Turnbull, P. C. B. et al., Med Microbiol Immunol. 177:293–303 (1988)). Neither vaccine has been examined in a human clinical efficacy trial. A high number of the recipients of the vaccine have reported some type of reaction to vaccination. The preponderance of these events were minor. Manufacturer labeling for the current Michigan Department of Public Health anthrax vaccine adsorbed (AVA) product cites a 30% rate of mild local reactions and a 4% rate of moderate local reactions with a second dose. The current complex dosing schedule for the AVA vaccine consists of 0.5 mL administered subcutaneously at 0, 2, and 4 weeks, and 6, 12, and 18 months, followed by yearly boosters. Animal studies examining the efficacy of available anthrax vaccines against aerosolized exposure have been performed. While some guinea pig studies question vaccine efficacy, primate studies have support its role. In recent work, rhesus monkeys immunized with 2 doses of the AVA vaccine were challenged with lethal doses of aerosolized B anthracis spores. All monkeys in the control group died 3 to 5 days after exposure, while the vaccinated monkeys were protected up to 2 years after immunization (Ivins, B. E. et al., Salisbury Med Bull Suppl. 87:125–126 (1996)). Another trial used the AVA vaccine in a 2-dose series with a slightly different dosing interval, and again found it to be protective in all rhesus monkeys exposed to lethal aerosol challenge (Pitt, M. L. M. et al., Salisbury Med Bull Suppl. 87:130 (1996)) Thus, available evidence suggests that two doses of the current AVA vaccine should be efficacious against an aerosol exposure to anthrax spores. In addition, a highly purified, minimally reactogenic, recombinant protective antigen vaccine has been investigated, using aluminum as well as other adjuvants. Other approaches include cloning the protective antigen gene into a variety of bacteria and Viruses, and the development of mutant, avirulent strains of B anthracis. One significant limitation on the use of vaccines is that existing vaccines provide no protection against a number of strains of B. anthracis.

Recent incidents, such as the suspected use of biological and chemical weapons during the Persian Gulf War, underscore the threat of biological warfare either on the battlefield or by terrorists. Anthrax has been the focus of much attention as a potential biological warfare agent for at least six decades, and modeling studies have shown the potential for use in an offensive capacity. Dispersal experiments with the simulant Bacillus globigii in the New York subway system in the 1960s suggested that release of a similar amount of B anthracis during rush hour would result in 10,000 deaths. On a larger scale, the World Health Organization estimated that 50 kg of B anthracis released upwind of a population center of 500,000 would result in up to 95,000 fatalities, with an additional 125,000 persons incapacitated (Huxsoll, D. L. et al., JAMA 262:677–679 (1989)). Both on the battlefield and in a terrorist strike, B. anthracis has the attribute of being potentially undetectable until large numbers of seriously ill individuals present with characteristic signs and symptoms of inhalational anthrax. Given these findings, efforts to prevent the disease or to ameliorate or treat its effects are of obvious importance. The U.S. military's current M17 and M40 gas masks provide excellent protection against the 1 to 5 $\mu$m particulates needed for a successful aerosol attack. Assuming a correct fit, these masks would be highly effective if in use at the time of exposure. Some protection might also be afforded by various forms of shelter. The preexposure use of the current AVA anthrax vaccine, which is approved by the U.S. Food and Drug Administration, appears to be an important adjunct. Results of primate studies also support the concept of postexposure antibiotic prophylaxis. One study showed that 7 of 10 monkeys given penicillin, 8 of 9 given ciprofloxacin, 9 of 10 treated with doxycycline, and all 9 receiving doxycycline plus postexposure vaccination survived a lethal aerosol challenge, with all animals receiving antibiotics for 30 days following exposure (Friedlander, A. M. et al., J Infect Dis. 167:1239–1242 (1993). Earlier research suggested that short courses of prophylactic antibiotics delayed but did not prevent clinical disease (Henderson, D. W. et al., J Hyg. 54:28–36 (1956). Accordingly, in the event of documented exposure, prolonged prophylactic antibiotic use, as well as vaccination, would be mandatory. In the biological warfare setting, the differential diagnosis of inhalational anthrax would include plague and tularemia. Fluoroquinolones also have activity against these diseases, supporting the use of ciprofloxacin and perhaps other drugs of this class as either a preexposure or postexposure measure.

It is therefore apparent that while certain prophylactic and treatment schemes may prove useful in preventing or ameliorating anthrax infections, there remains a compelling need to improve the arsenal of techniques and agents available for this purpose.

Accordingly, it is an object of the invention described herein to provide compositions that are capable of precisely targeting acute responses to Anthrax Lethal Factor without producing significant undesirable side effects.

This and other objects will be apparent from consideration of the specification as a whole.

DISCLOSURE OF THE INVENTION

The present invention provides methods, compounds and compositions for treating anthrax infections by inhibiting anthrax lethal factor activity. In one aspect, the invention provides a compound in accordance with the formula:

$$\text{R1-N(OH)-C(=O)-C(R4)=N-C(R3)=C(R2)}$$

Wherein
R1, R2, R3 and R4 are each independently selected from
H, hydroxyl, alkoxy, alkylthio,
small alkyl (C1–C10) (optionally C1–C6) (optionally substituted with alkyl, cycloalkyl fluoro, aryl, heteroaryl, alkylthio, arylthio, cyano, OR6, OC=OR6, C=O—OR7, or C=O—NR8R9),
phenyl and mono and disubstituted (at positions 3 and 4) phenyl (wherein the phenyl ring is independently substituted with alkyl, trifluoromethyl, mono and di halogen atoms, alkylthio, alkoxy, nitro, cyano, morphilino, cyclohexyl, phenyl, phenolic, dioxymethylene, nitro, acetylamino);
heteroaryl (optionally substituted with alkyl, halogen, alkylthio, alkoxy, or nitro),
cycloalkyl (C3–C10) (optionally substituted with alkyl, fluoro, aryl, heteroaryl, alkylthio, arylthio, cyano, OR5, OC=OR5, C=O—OR6, or C=O—NR7R8)
alkenyl (C1–C10) (optionally substituted with alkyl, fluoro, aryl, heteroaryl, alkylthio, arylthio, cyano, OR5, OC=OR5, C=O—OR6, or C=O—NR7R8)
alkadienyl (C1–C10) (optionally substituted with alkyl, fluoro, aryl, heteroaryl, alkylthio, arylthio, cyano, OR5, —OC=OR5, —C=O—OR6, C=O—NR7R8)
cycloalkenyl (C4–C10), optionally substituted with alkyl, fluoro, aryl, heteroaryl, alkylthio, arylthio, cyano, OR5, —OC=OR5, —C=O—OR6, C=O—NR7R8
bicycloalkyl (C5–C12), optionally substituted with alkyl, fluoro, aryl, heteroaryl, alkylthio, arylthio, cyano, OR5, —OC=OR5, —C=O—OR6, C=O—NR7R8
tricycloalkyl (C8–C14), optionally substituted with alkyl, fluoro, aryl, heteroaryl, alkylthio, arylthio, cyano, OR5, —OC=OR5, —C=O—OR6, C=O—NR7R8
where
R5 is
alkyl (C1–C10), optionally substituted with alkyl, keto, fluoro, alkoxy, alkylthio, aryl, heteroaryl, cyano, aryloxy, cycloalkyl;
aryl, optionally substituted with alkyl, keto, fluoro, alkoxy, alkylthio, cyano, aryloxy;
heteroaryl, optionally substituted with alkyl, keto, fluoro, alkoxy, alkylthio, cyano, aryloxy;
cycloalkyl, optionally substituted with alkyl, keto, fluoro, alkoxy, alkylthio, aryl, heteroaryl, cyano:
R6 is
alkyl (C1–C10), optionally substituted with alkyl, keto, fluoro, alkoxy, alkylthio, aryl, heteroaryl;
aryl, optionally substituted with alkyl, keto, fluoro, alkoxy, alkylthio;
heteroaryl, optionally substituted with alkyl, keto, fluoro, alkoxy, alkylthio;
cycloalkyl, optionally substituted with alkyl, keto, fluoro, alkoxy, alkylthio, aryl, heteroaryl;
R7 is
alkyl (C1–C10), optionally substituted with alkyl, keto, fluoro, alkoxy, alkylthio, aryl, heteroaryl;
aryl, optionally substituted with alkyl, keto, fluoro, alkoxy, alkylthio;
heteroaryl, optionally substituted with alkyl, keto, fluoro, alkoxy, alkylthio;
cycloalkyl, optionally substituted with alkyl, keto, fluoro, alkoxy, alkylthio, aryl, heteroaryl; and
R8 is
alkyl (C1–C10), optionally substituted with alkyl, keto, fluoro, alkoxy, alkylthio, aryl, heteroaryl;
aryl, optionally substituted with alkyl, keto, fluoro, alkoxy, alkylthio;
heteroaryl, optionally substituted with alkyl, keto, fluoro, alkoxy, alkylthio;
cycloalkyl, optionally substituted with alkyl, keto, fluoro, alkoxy, alkylthio, aryl, heteroaryl.

Such compounds and compositions will be found suitable for use as specific inhibitors of anthrax lethal factor activity for the prophylaxis and treatment of anthrax infections.

DETAILED DESCRIPTION OF THE INVENTION

Figure 1:
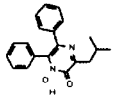
FIG. 1 is a graphic depiction of selected compounds of the present invention.
Figure 1:
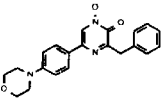
Figure 1:
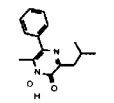
Figure 1:
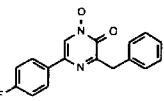
Figure 1:
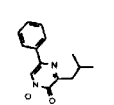
Figure 1:
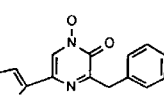
Figure 1:
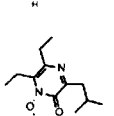
Figure 1:
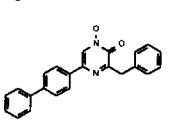
Figure 1:
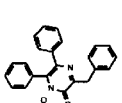
Figure 1:
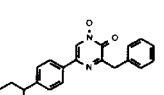
Figure 1:
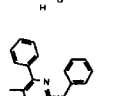
Figure 1:
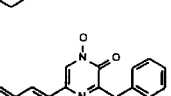
Figure 1:
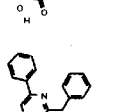
Figure 1:
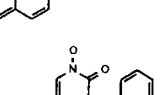
Figure 1:
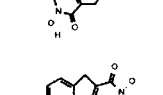
Figure 1:
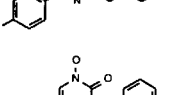
Figure 1:
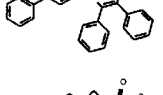
Figure 1:
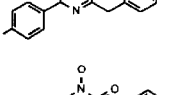
Figure 1:
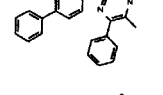
Figure 1:
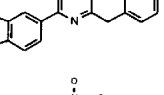
Figure 1:
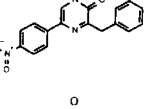
Figure 1:
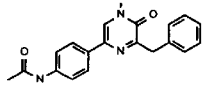
Figure 1:
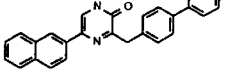
Figure 1:
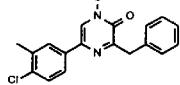
Figure 1:
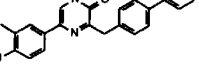
Figure 1:
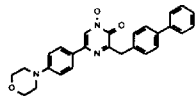
Figure 1:
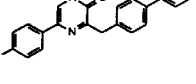
Figure 1:
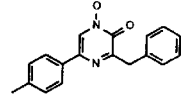
Figure 1:
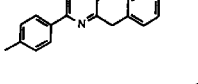
Figure 1:
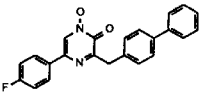
Figure 1:
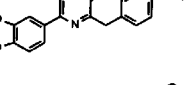
Figure 1:
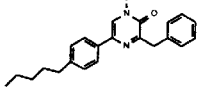
Figure 1:
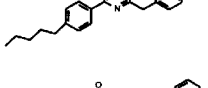
Figure 1:
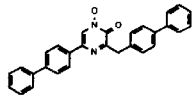
Figure 1:
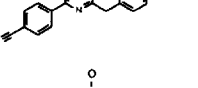
Figure 1:
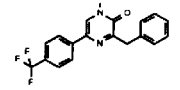
Figure 1:
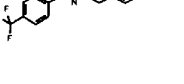
Figure 1:
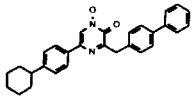
Figure 1:
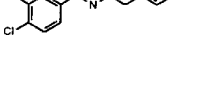
Figure 1:
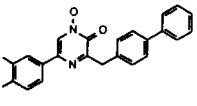

The present invention provides methods, compounds and compositions for treating anthrax infections by inhibiting anthrax lethal factor (ALF) activity. The novel compositions for use herein are ALF inhibitors. These substances function by binding to the ALF cleavage site, and preventing the ALF from catalyzing its physiological substrate. ALF inhibitors are useful, either alone or together with other therapeutic compositions, in the prevention and treatment of anthrax infections. Although the term "infection" is ordinarily used in its epidemiological sense, it will readily be recognized that "infections" by *Bacillus anthracis* spp., or invasions by ALF, can occur naturally or be purposefully induced.

Anthrax toxin, produced by *Bacillus anthracis*, is composed of three proteins: Protective antigen, edema factor and ALF. Protective antigen (PA) is an 83 kd protein that binds to specific cell surface receptors and is then proteolytically activated to a 63 kd fragment (PA63), which forms a membrane channel that mediates entry of edema factor (EF) or anthrax lethal factor (ALF) into the cell. PA combines with either EF, an 89 kd protein, to form edema toxin, or ALF, a 90 kd protein, to form lethal toxin (Leppla, S. H. et al., *Salisbury Med Bull Suppl.*, 68:41–43 (1990)). The respective toxins are then transported across the cell membrane, and the factors are released into the cytosol where they exert their effects. EF, a calmodulin-dependent adenylate cyclase, acts by converting adenosine triphosphate to cyclic adenosine monophosphate. Intracellular cyclic adenosine monophosphate levels are thereby increased, leading to the edema characteristic of the disease (Leppla, S. H., *Proc Natl Acad Sci USA* 79:3162–3166 (1982)).

The action of ALF, the dominant virulence factor produced by *Bacillus anthracis*, and believed to be a metalloprotease, is less well understood. Lethal toxin has been demonstrated at high concentration to lyse macrophages, while inducing the release of tumor necrosis factor and interleukin 1 at lower concentrations (Hanna, P. C. et al., *Proc Natl Acad Sci USA* 90:10198–10201 (1993); Freidlander, A. M., *J Biol Chem*. 261:7123–7126 (1986)). ALF is a 776 amino acid protein that contains a putative zinc-binding site (HEFGF) at residues 686–690, a characteristic of metalloproteases. Mutation of the H or E residues is reported to inactivate ALF, and reduces its zinc-binding activity.

One useful approach to providing ag components of the hydroxamic acid structures will be expected to retain the ALF inhibitor activity.

SYNTHESIS OF INHIBITOR COMPOUNDS OF THE INVENTION

In general, the compounds of the present invention can be prepared in accordance with chemical synthetic protocols well known to those of skill in this art. One desirable category of such techniques is know by the generic term "combinatorial chemistry." Such techniques are well know in the art, and can be generally summarized as follows: For example, preparation of libraries can be by the "split synthesis" method, as described in Gallop et al., *J. Med. Chem.*, 37:1233–1251 (1994). The split synthesis procedure involves dividing a resin support into n equal fractions, in a separate reaction carry out a single reaction to each aliquot, and then thoroughly mixing all the resin particles together. Repeating the protocol for a total of x cycles can produce a stochastic collection of up to $n^x$ different compounds. An alternative format is by preparing sublibraries in the $O_3O_2X_1$ format, wherein two positions on the compounds, $O_3$ and $O_2$ are explicitly defined and a third position, $X_1$, varies. Such sublibraries can be conveniently prepared by the tea-bag technique, as is known in the art, and described, for example in U.S. Pat. No. 4,631,211 and Houghten et al., *Proc. Natl. Acad. Sci.*, 82:5131–5135 (1985).

Alternatively, or in addition thereto, the iterative selection and enhancement process of screening and sublibrary resynthesis can be employed. For example, a sublibrary of various R1 substituents can be screened to select the most active R1 substituent. The compound having the most active R1 is then resynthesized and with the R1 position being defined, a new R2 position mixture library is prepared, screened, and the most active R2 selected. The above process can then be repeated to identify the most active R substituents on the backbone structure.

In yet another approach, the positional scanning technique, only a single position is defined in a given sublibrary and the most preferred substituent at each position of the compound is identified.

The advantage of synthetic combinatorial libraries (SCLs) made up of mixtures of tens of millions of different compounds is that they can be used to rapidly identify individual, active compounds without the need to individually synthesize, purify, and test every single compound. Since the libraries are in solution (i.e., not attached to a bead, pin, phage, glass, etc.) they can be screened in virtually any assay system.

Solution phase combinatorial chemistry methods can be used when the product can be separated from side products and starting materials through rapid techniques. Examples of these are: (1) selective precipitation of product and removal of byproducts and precursors by washing, (2) selective removal of side products and starting materials using chemically reactive polymers and/or ion exchange polymers ("scavenge"), (3) selective binding of product to a chemically reactive polymer, followed by removal of the product through a second chemical reaction ("capture") (4) selective binding of product to an ion exchange polymer, followed by removal with acid, base, or high salt buffer ("capture"), and (5) selective solubilization of product. Solution phase combinatorial chemistry approaches are covered in a recent set of reviews (*Tetrahedron*, 54:3955–4150 (1998)).

The synthetic approaches described in Examples 1–40 can be optimally carried out using solution phase combinatorial chemistry. Several reactions are carried out simultaneously using a multiple reaction vessel block such as, but not limited to, the Charybdis Calypso™ temperature controlled blocks, with gas manifolds to maintain an argon or nitrogen atmosphere. Alternately, the reactions can be carried out simultaneously in multiple vials filled with argon or nitrogen and fitted with magnetic stirbars and polytetrafluoroethylene-lined, sealed caps, by heating and stirring them simultaneously in a magnetic stirrer/heater such as, but not limited to, the Pierce ReactTherm™ III Heating/Stirring Module. The products are isolated by addition of water and filtration using a system such as, but not limited to, the Charybdis Calypso™ filtration block or polypropylene syringes fitted with filter disks made from polyethylene, polytetrafluoroethylene, or glass and attached to a vacuum manifold.

By way of illustration of basic techniques for the synthesis of compounds within the scope of the present invention, specific examples are provided below which will prove exemplary of such synthetic techniques.

Determination of ALF Inhibitor Biological Activity

There are numerous assays techniques available which can be adapted to routinely identify compounds that display activity as ALF inhibitors. In this manner, highly sensitive, non-radioactive probes are found very useful for high throughput screening of potential small molecule ALF antagonists.

In order to perform such assays, two procedures have been devised:

Gel Assay

ALF Cleavage Assay—Western Blot
Pre-incubation of Inhibitors with ALF:
 7 μL of ALF (1 μg/mL) is pipetted into each vial, them 1 μL of DMSO or 1 μL of sample is added to the vials. The vials are vertexed and centrifuged for one minute. The vials are placed in a 30° C. water incubator for 30 minutes.
Addition of His Tagged Mek-1:
 After 30 minutes, the samples are taken from the incubator, opened and 2 μL of His-tagged Mek-1 (0.5 μg/mL) is added to each of the vials. The vials are vertexed and centrifuged for one minute and transferred into 30° C. water incubator for 30 minutes.
Quenching the Assay:
 After 30 minutes, the samples are taken from the incubator and 15 μL of SDS sample buffer (62.5 mM Tris-HCl, pH 6.8, 2% w/v SDS, 10% glycerol, 50 mM dithiothreitol (DTT), 0.1% w/v bromophenol blue) is added to each of the vials. The samples are vertexed and, if desired, stored at −20° C. prior to further analysis.
Western Blots:
 SDS-polyacrylamide gel electrophoresis (SDS-PAGE) is performed on the samples by adding 44 μL of SDS sample buffer, boiling for 5 minutes, and running 30 μL aliquots on a 14% tris-glycine gel. The gel is then transferred onto nitrocellulose. The blot is rinsed twice with water, and the blocked with PBS containing 3% nonfat dry milk (PBS-MLK) for 20 minutes at room temperature.
 The blot is then incubated with a 1:1000 dilution of α-Mouse MEK1-NT (or CT), diluted in PBS-MLK, overnight at 4° C. After incubation, the blot is washed twice with water, and incubated in anti-rabbit IgG linked to horseradish peroxidase, 1:2500 in PBS-MLK for 90 minutes at room temperature with agitation. The blot is again washed with water twice, then in PBS-00.5% Tween 20 for 3–5 minutes. The blot is rinsed in 4–5 changes of water, and enhanced chemiluminescence (ECL) is used to detect cleavage. Scion Image software is used to quantitate bands per lane and to quantitate control bands.

Plate Assay

Anthrax Lethal Factor Plate Assay Protocol

Materials:

ALF Protease: 1 mg/mL (20 µL/tube)

Substrate (GST-MEK1 fusion protein): 0.25 mg/mL (Upstate Biotechnology)

Reaction Buffer: 50 mM MOPS, pH 7.2

Compounds in DMSO solution are diluted to 0.5 mM for screening

I. Solution Reactions:

1). A Costar EIA/RIA plate (1/2 area flat bottom, 96-well) is blocked with 100 µL Superblock for 1 hour.

2). Master mixtures are added to each well of the plate, and 0.4 µL of test compound is added to each well. Substrates are added last. The wells are covered with parafilm and the plate is incubated at 37° C. for 16 hours.

Note: Reactions are carried out in 20 µL volume containing 0.2 µg GST-MEK1, 0.5 µg ALF in 50 mM MOPS buffer, pH 7.2 in the presence of 2.5 mg/mL BSA.

| Cpd | H$_2$O | 1 M buffer | 5% BSA | ALF | Substrate |
|---|---|---|---|---|---|
| 0.4 µL | 16.3 µL | 1 µL | 1 µL | 0.5 µL | 0.8 µL |

Negative controls are the reaction mixtures without addition of compounds; Positive controls are the reaction mixtures without additions of compounds and ALF.

II. Plate Assay Protocol:

1). Coating. 100 µL 2 µg/mL rabbit anti-MEK1 (C-18) (Santa Cruz Biotech, carrier-free) are coated in 50 mM carbonate buffer, pH 8.1 in a 96-well plate, covered with parafilm and incubated at 4° C. for 16 hours.

2). Blocking. 200 µL SuperBlock is added, and incubated for 30 min.

3). Loading. Add 41 µL SuperBlock/Tween and 91 µL reaction mixture in each well. Incubate at RT for 1.5 hours.

4). Washing. 3 times in 200 µL TBST buffer.

5). Detection. 50 µL 0.5 µg/mL Eu-Anti GST antibody in SuperBlock/Tween are added, and incubated at RT for 1 hour.

6). Washing. 3 times in 200 µL TBST buffer.

7). Reading. Add 100 µL of Enhancement solution. Shake for 10 minutes and read Europium counts.

Prophylaxis and Treatment of Infectious Responses

The therapeutically effective amounts of the present ALF inhibitor will be a function of many variables, including the affinity of the inhibitor for the ALF, any residual cytotoxic activity exhibited by competitive antagonists, the route of administration, the clinical condition of the patient, and whether the inhibitor is to be used for the prophylaxis or for the treatment of acute response episodes. The molar dose of ALF inhibitor will be expected to vary about from 0.001 to 10 times the maximum tolerated molar dose of ALF, although as noted above this range will be subject to a great deal of therapeutic discretion. It is to be expected that concentrations of ALF localized at the sites of infection may exceed the whole body maximum therapeutic dose. Assay of the ALF concentration in infiltrates will provide guidance as to the amount of ALF inhibitor to be employed, particularly if localized administration is practical. The key factor in selecting an appropriate dose is the result obtained: If the patient's response does not at least partially resolve within hours after administration, the dose should be gradually elevated until the desired effect is achieved. Also, relatively higher doses will be initially needed for the treatment for acute episodes, i.e., for patients in acute anthrax infection.

In practicing the method of the present invention, the therapeutic preparation will be administered to a patient in need of ALF inhibitory treatment at a therapeutically effective dosage level. The lowest effective dosage levels can be determined experimentally by initiating treatment at higher dosage levels and reducing the dosage level until relief from reaction is no longer obtained. Generally, therapeutic dosage levels will range from about 0.01–100 μg/kg of host body weight.

The present ALF inhibitor can also administered in conjunction with other antibiotic agents used in or proposed for the treatment of individual conditions as appropriate, e.g. cephalosporin antibiotics, and the like. However, when employed together with ALF inhibitors, these agents may be employed in lesser dosages than when used alone.

Where combinations are contemplated, it is not intended that the present invention be limited by the particular nature of the combination. The present invention contemplates combinations as simple mixtures as well as chemical hybrids. One example of the latter is where the present compound is covalently linked to a pharmaceutical such as an antibiotic, or where two or more compounds are joined. For example, covalent binding of the distinct chemical moieties can be accomplished by any one of many commercially available cross-linking compounds.

In view of the therapeutic urgency attendant acute episodes, the ALF inhibitor should be intravenously infused or introduced at the lesion immediately upon the development of symptoms or serological evidence of ALF activity. However, prophylaxis is suitably accomplished by intramuscular or subcutaneous administration. In this regard, the compositions are prepared as injectables, either as liquid solutions or suspensions; solid forms suitable for solution in, or suspension in, liquid prior to injection may also be prepared. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

It is not intended that the present invention be limited by the particular nature of the therapeutic preparation. For example, such compositions can be provided together with physiologically tolerable liquid, gel or solid carriers, diluents, adjuvants and excipients. Such compositions are typically prepared as sprays (e.g. intranasal aerosols) for topical use. However, they may also be prepared either as liquid solutions or suspensions, or in solid forms including respirable and nonrespirable dry powders. Oral formulations (e.g. for gastrointestinal administration) usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compounds of the present invention are often mixed with diluents or excipients which are physiologically tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

The following Examples serve to illustrate certain preferred embodiments and aspects of the present invention and are not to be construed as limiting the scope thereof. The structures of various of the disclosed compounds will be found depicted in FIG. 1.

EXPERIMENTAL

In the experimental disclosure which follows, all weights are given in grams (g), milligrams (mg), micrograms (µg), nanograms (ng), or picograms (pg), all amounts are given in moles, millimoles (mmol), micromoles (µmol), nanomoles (nmol), picomoles (pmol), or femtomoles (fmol), all concentrations are given as percent by volume (%), proportion by volume (v:v), molar (M), millimolar (mM), micromolar (µM), nanomolar (nM), picomolar (pM), femtomolar (fM), or normal (N), all volumes are given in liters (L), milliliters (mL), or microliters (µL), and linear measurements are given in millimeters (mm), or nanometers (nm) unless otherwise indicated.

The following Examples demonstrate the practice of the present invention in synthesizing compounds according to the invention, generally as depicted in FIG. 1, and in methods by which drugs having the formulas shown can be readily identified by routine assay procedures to demonstrate that they possess the desired activity. All mass spectra are determined using cation electrospray using a Hewlett Packard 1100 series MSD mass spectrometer with a fragmenter voltage setting of 50 volts.

Synthesis of 3, 5, 6-substituted 1-hydroxy-2-oxo-1,2 dihydropyrazines: These compounds are synthesized using one of the two procedures from *Chem. Pharm. Bull.* 36 2323–2330 (1988) that are illustrated as follows:

Example 1

Compound 1

Method A: 3-isoprpyl-5,6dipheny-1-1-hydroxy-2-oxo-1,2-dihydropyrazine is prepared by mixing diphenylethane dione (90 mg) and leucinehydroxamic acid (73 mg) in a mixture of ethanol and water (1:1) (5 mL) and heating to 80° C. and stirred overnight. The solids that are formed are filtered and recrystallized from hot ethanol. Yield: 45 mg (19%).

$H^1$NMR: (300 MHz, $CDCl_3$): 7.38 δ (5H m); 7.19 δ (5H m); 2.89 δ (2H d); 2.38 δ (1H m); 1.04 δ (6H d).

Example 2

Compound 2

Method B: 3-isopropyl-5,6diethyl-1-hydroxy-2-oxo-1, 2dihydropyrazine is prepared by dissolving leucine hydroxamic acid (73 mg) in a mixture of methanol/water (1/1) (5 mL) and cooling to −30° C. and mixing with 1,4-hexanedione (57 mg) at −30° C. To this mixture, a very dilute solution of (~0.5M NaOH) is added to maintain the pH above 7.0 but not greater than 8.5 for about one hour. The temperature is then slowly brought to room temperature, and the mixture is stirred at room temperature overnight. The solid that is formed is filtered and recrystallized from ethanol/water mixture. Yield 25 mg.

$H^1$ NMR: (300 MHz, DMSO-D6): 3.6 δ (2H, m); 3.4 δ (2H, q); 3.2 δ (2H, d); 1.4 δ (4H, m); 1.1 δ (3H, t) 0.9 δ (6H, t).

Example 3

Compound 3

1-hydroxy-6-methyl-3-(2-methylpropyl)-5-phenylhydropyrazin-2-one is prepared by method B using leucine hydroxamic acid (73 mg) and 1-phenyl-1,2-propanedione (74 mg). Yield: 23%.

NMR: (300 MHz, $CDCl_3$): 8.6 δ (1H, b); 7.47 δ (5H, m); 2.8 δ (2H, d); 2.54 δ (3H, s); 2.28 δ (1H, m); 0.99 δ (6H, d).

Example 4

Compound 4

1-hydroxy-3-(2-methylpropyl)-5-phenylhydropyrazin-2-one is prepared by method B using leucine hydroxamic acid (73 mg) and phenylglyoxal (76 mg). Yield: 23%.

NMR: (300 MHz, $CDCl_3$): 8.6 δ (1H, b); 7.99 δ (1H, m); 7.79 δ (2H, m); 7.43 δ (3H, m); 2.82 δ (2H, d); 2.32 δ (1H, m); 0.99 δ (6H, d).

Example 5

Compound 5

1-hydroxy-5,6-diphenyl-3-benzylhydropyrazin-2-one is prepared by method A using dl-phenylalanine hydroxamic acid (90 mg) and diphenylethane dione (90 mg). Yield: 20%.

NMR: (300 MHz, DMSO-D6): 7.39 δ (8H, m); 7.23 δ (2H, m); 7.14 δ (5H, m); 4.15 δ (2H, s). ESI MS, Observed $(M+H)^+=355$ Example 6

Compound 6

1-hydroxy-6-methyl-5-phenyl-3-benzylhydropyrazin-2-one is prepared by method A using dl-phenylalanine hydroxamic acid (90 mg) and 1-phenyl-1,2-propanedione (74 mg). Yield: 19%.

NMR: (300 MHz, DMSO—D6): 7.47 δ (4H, m); 7.28 δ (6H, m); 4.06 δ (2H, s); 2.36 δ (3H, s). ESI MS, Observed $(M+H)^+=293$ Example 7

Compound 7

1-hydroxy-5-phenyl-3-benzylhydropyrazin-2-one is prepared by method A using dl-phenylalanine hydroxamic acid (90 mg) and phenylglyoxal (67 mg). Yield: 25%.

NMR: (300 MHz, DMSO-D6):8.52 δ (1H, s); 7.88 δ (2H, d); 7.35 δ (8H, m); 4.10 δ (2H, s). ESI MS, Observed $(M+H)^+=279$ Intermediate Compound 8

$N^{\alpha}$-$^{tert}$Butyloxycarbonyl-4-phenyl-pehnylalanine-O-benzyl-hydroxamic acid is prepared by coupling 3-(4- biphenylyl)-N-(tert-butoxycarbonyl)-L-alanine (1.02 g, 3 mmols) with O-benzylhydroxalyamine hydrochloride (0.525 g, 3.3 mmols) using HATU (3.3 mmols), HOAT (3.3 mmols) and DIEA (6.6 mmols) in DMF (5 mL). The mixture is stirred overnight. DMF is rotovaped under vacuum. The residue is taken up in EtOAc, and the EtOAc is washed with 1M HCl (2×25 mL), saturated $NaCO_3$ (2×25 mL) and finally brine solution (2×25 mL). The EtOAc solution is dried over anhydrous sodium sulphate and rotovaped, and the residue is triturated with hexane to yield a solid. Yield 0.95 g (71%).

NMR: (300 MHz, $CDCl_3$): 8.61 δ (1H, s); 7.55 δ (4H, m); 7.43 δ (2H, m); 7.28 δ (6H, m); 5.09 δ (1H, d); 4.85 δ (1H, m); 4.68 δ (1H, m); 4.2 δ (1H, q); 3.05 δ (2H, m); 1.38 δ (9H, s).

Intermediate Compound 9

$N^{\alpha}$-$^{tert}$Butyloxycarbonyl-4-phenyl-pehnylalanine-hydroxamic acid is prepared by catalytic hydrogenation of Intermediate Compound 8 (0.85 g) in methanol using 10% Pd/C and a hydrogen balloon. After the hydrogenation, the Pd/C is filtered and the solvent is rotovaped to yield a solid. Yield: 0.65 g (95%).

NMR: (300 MHz, $CDCl_3$): 10.7 δ (1H, b); 8.9 δ (1H, s); 8.7 δ (4H, m); 8.4 δ (2H, m); 8.23 δ (3H, m); 4.1 δ (1H, m); 2.85 δ (2H, s); 1.38 δ (9H, s).

Intermediate Compound 10

4-phenyl-pehnylalanine-hydroxamic acid is prepared by treating Intermediate Compound 9 (0.64 g) with 4N HCl/Dioxane for 30 minutes. The dioxane is rotovaped and the residue is triturated with ether and dried under vacuum. Yield: 0.42 g (91%). This is used without further purification.

Example 8

Compound 11

3-(4'-phenyl)-benzyl-5,6diphenyl-1-hydroxy-2-oxo-1,2-dihydropyrazine is prepared using method A from Intermediate Compound 10 (146 mg) and diphenylethane dione (90 mg). Yield: 29%.

NMR: (300 MHz, DMSO-D6):7.95 δ (8H, d); 7.81 δ (4H, m); 7.64 δ (7H, m); 3.36 δ (2H, m). ESI MS, Observed $(M+H)^+=391$ Example 9

Compound 12

3-(4'-phenyl)-benzyl-5-phenyl-6-methyl-1-hydroxy-2-oxo-1,2-dihydropyrazine is prepared using method A from Intermediate Compound 10 (146 mg) and 1-phenylL-1,2-propanedione (74 mg). Yield: 23%.

NMR: (300 MHz, DMSO-D6):7.6 δ (6H, m); 7.4 δ (8H, m); 4.1 δ (2H, s); 2.32 δ (3H, s). ESI MS, Observed $(M+H)^+=369$ Example 10

Compound 13

3-(4'-phenyl)-benzyl-5phenyl-1-hydroxy-2-oxo-1,2-dihydropyrazine is prepared using method A from Intermediate Compound 10 (146 mg) and phenylglyoxal (67 mg). Yield: 22%.

NMR: (300 MHz, DMSO-D6):8.54 δ (1H, s); 7.89 δ (2H, d); 7.6 δ (4H, t); 7.46 δ (8H, m); 4.18 δ (2H, s). ESI MS, Observed $(M+H)^+=355$ Example 11

Compound 14

1-hydroxy-5-(4-morpholin-4-ylphenyl)-3-benzylhydropyrazin-2-one is prepared by method A using dl-phenylalanine hydroxamic acid (135 mg) and 4-morphilinophenylglyoxal (164 mg). Yield: 35%.

NMR: (300 MHz, DMSO-D6): ): 8.54 δ (1H, s); 7.8 δ (2H, d); 7.3 δ (5H, m); 7.0 δ (2H, d); 4.05 δ (2H, s); 3.75 δ (4H, m); 3.1 δ (4H, m). ESI MS, Observed $(M+H)^+=364$ Example 12

Compound 15

5-(4-fluorophenyl)-1-hydroxy-3-benzylhydropyrazin-2-one is prepared by method A using dl-phenylalanine hydroxamic acid (135 mg) and 4-fluorophenylglyoxal (114 mg). Yield: 2%.

NMR: (300 MHz, DMSO-D6): ): 8.45 δ (1H, s); 7.92 δ (2H, m); 7.25 δ (7H, m); 4.1 δ (2H, m). ESI MS, Observed $(M+H)^+=297$ Example 13

Compound 16

1-hydroxy-3-benzyl-5-(2-thienyl)hydropyrazin-2-one is prepared by method B using dl-phenylalanine hydroxamic acid (135 mg) and 2-thiophenelglyoxal (105 mg). Yield: 23%.

NMR: (300 MHz, DMSO-D6): ):8.55 δ (1H,s); 7.6 δ (2H, m); 7.3 δ (4H, m); 7.25 δ (1H, m); 7.1 δ (1H, m); 4.1 δ (2H, s). ESI MS, Observed $(M+Na)^+=307$ Example 14

Compound 17

1-hydroxy-3-benzyl-5-(4-phenylphenyl)hydropyrazin-2-one is prepared by method A using dl-phenylalanine hydroxamic acid (135 mg) and 4-biphenylglyoxal (158 mg). Yield: 32%.

NMR: (300 MHz, DMSO-D6): ):8.4 δ (1H, s); 8.05 δ (2H, m); 7.8 δ (4H, m); 7.4 δ (3H, m); 7.2 δ (5H, m); 4.1 δ (2H, s). ESI MS, Observed $(M+Na)^+=377$ Example 15

Compound 18

5-(4-cyclohexylphenyl)-1-hydroxy-3-benzylhydropyrazin-2-one is prepared by method A using dl-phenylalanine hydroxamic acid (135 mg) and 4-cyclohexylphenylglyoxal (162 mg). Yield: 35%.

NMR: (300 MHz, DMSO-D6): 8.45 δ (1H, s); 7.8 δ (1H, d); 7.3 δ (9H, m); 4.1 δ (2H, s); 1.82 δ (6H, m); 1.4 δ (5H, m). ESI MS, Observed $(M+Na)^+=383$ Example 16

Compound 19

1-hydroxy-5-(2-naphthyl)-3-benzylhydropyrazin-2-one is prepared by method A using dl-phenylalanine hydroxamic acid (135 mg) and 2-naphtylglyoxal (138 mg). Yield: 19%.

NMR: (300 MHz, DMSO-6): 8.65 δ (1H, s); 8.42 δ (1H, d ); 8.06 δ (1H, m); 7.85 δ (3H, m); 7.5 δ (2H, m); 7.38 δ (2H, m); 7.3 δ (2H, m); 7.2 δ (1H, m); 4.05 δ (2H, s). ESI MS, Observed $(M+Na)^+=351$

Example 17

Compound 20

5-(4-bromophenyl)-1-hydroxy-3-benzylhydropyrazin-2-one is prepared by method A using dl-phenylalanine hydroxamic acid (135 mg) and 4-bromophenylglyoxal (160 mg). Yield: 35%.

NMR: (300 MHz, DMSO-D6): 8.56 δ (1H, s); 7.85 δ (2H, m); 7.6 δ (2H, m); 7.3 δ (4H, m); 7.22 δ (1H, m); 4.3 δ (2H, s). ESI MS, Observed $(M+Na)^+=381$

Example 18

Compound 21

1-hydroxy-5-(4-hydroxyphenyl)-3-benzylhydropyrazin-2-one is prepared by method B using dl-phenylalanine hydroxamic acid (135 mg) and 4-hydroxy-phenylglyoxal (113 mg). Yield: 18%.

NMR: (300 MHz, DMSO-D6):8.36 δ (1H, s); 7.7 δ (2H, m); 7.3 δ (8H, m), 6.8 δ (1H, m); 4.05 δ (2H, s). ESI MS, Observed $(M-H)=293$

Example 19

Compound 22

5-(2H-benzo[d]1,3-dioxolen-5-yl)-1-hydroxy-3-benzylhydropyrazin-2-one is prepared by method A using dl-phenylalanine hydroxamic acid (135 mg) and 3,4-methylenedioxyphenylglyoxal (134 mg). Yield: 25%.

NMR: (300 MHz, DMSO-D6): 8.42 δ (1H, s); 7.4 δ (2H, m); 7.3 δ (4H, m); 7.2 δ (1H, m); 6.95 δ (1H, m); 6.05 δ (2H, s); 4.05 δ (2H, s). ESI MS, Observed $(M+Na)^+=345$

Example 20

Compound 23

1-hydroxy-5-(4-nitrophenyl)-3-benzylhydropyrazin-2-one is prepared by method A using dl-phenylalanine hydroxamic acid (135 mg) and 4-nitrophenylglyoxal (135 mg). Yield: 26%.

NMR: (300 MHz, DMSO-D6): 8.82 6(1H, s); 8.3 δ (2H, d); 8.19 δ (2H, d); 7.36 δ (4H, m); 7.25 δ (1H, M); 4.08 δ (2H, s). ESI MS, Observed $(M+Na)^+=346$

Example 21

Compound 24

4-[4-hydroxy-5-oxo-6-benzyl-4-hydropyrazin-2-yl] benzenecarbonitrile is prepared by method A using dl-phenylalanine hydroxamic acid (135rmg) and 4-cyano phenylglyoxal (120 mg). Yield: 35%.

NMR: (300 MHz, DMSO-D6):8.78 δ (1H, s); 8.16 δ (2H, d); 7.84 δ (2H, d); 7.3 δ (4H, m); 7.24 δ (1H, m); 4.16 δ (2H, s). ESI MS, Observed $(M+Na)^+=326$

Example 22

Compound 25

N-{4-[4-hydroxy-5-oxo-6-benzyl-4-hydropyrazin-2-yl] phenyl}acetamide is prepared by method A using dl-phenylalanine hydroxamic acid (135 mg) and 4-(N-acetylamino)phenylglyoxal (144 mg). Yield: 17%.

NMR: (300 MHz, DMSO-D6):10.05 δ (1H, s); 8.4 δ (1H, s); 7.8 δ (2H, d); 7.64 δ (2H, d); 7.3 δ (5H, m); 4.04 δ (2H, s); 2.0 δ (3H, s). ESI MS, Observed $(M+Na)^+=358$

Example 23

Compound 26

1-hydroxy-5-(4-morpholin-4-ylphenyl)-3-[(4-phenylphenyl)methyl] hydropyrazin-2-one is prepared by method A using Intermediate Compound 10 (110 mg) and 4-morphilinophenylglyoxal (164 mg). Yield: 19%.

NMR: (300 MHz, DMSO-D6):8.56 δ (1H, s); 7.74 δ (2H, d); 7.74 δ (5H, m); 7.4 δ (5H, m); 6.96 δ (1H, m); 4.05 δ (2H, s); 3.7 δ (4H, m); 3.1 δ (4H, m). ESI MS, Observed $(M+H)^+=$

Example 24

Compound 27

5-(4-fluorophenyl)-1-hydroxy-3-[(4-phenylphenyl) methyl]hydropyrazin-2-one is prepared by method A using Intermediate Compound 10 (110 mg) and 4-fluorophenylglyoxal (61 mg). Yield: 25%.

NMR: (300 MHz, DMSO-D6):8.54 δ (1H, s); 7.94 δ (2H, m); 7.6 δ (4H, m); 7.4 δ (4H, m); 7.36 δ (1H, m); 7.24 δ (2H, m); 4.1 δ (2H, s). ESI MS, Observed $(M+Na)^+=395$

Example 25

Compound 28

1-hydroxy-5-(4-phenylphenyl)-3-[(4-phenylphenyl) methyl]hydropyrazin-2-one is prepared by method A using Intermediate Compound 10 (110 mg) and 4-biphenylglyoxal (84 mg). Yield: 22%.

NMR: (300 MHz, DMSO-D6):8.6 δ (1H, s); 8.0 δ (2H, d); 7.7 δ (4H, m); 7.6 δ (4H, m); 7.1 δ (3H, m); 4.10 δ (2H, s).

Example 26

Compound 29

5-(4-cyclohexylphenyl)-1-hydroxy-3-[(4-phenylphenyl) methyl] hydropyrazin-2-one is prepared by method A using Intermediate Compound 10 (110 mg) and 4-cyclohexylphenylglyoxal (87 mg). Yield: 20%.

NMR: (300 MHz, DMSO-D6):8.62 δ (1H, s); 7.8 δ (2H, m); 7.58 δ (5H, m); 7.4 δ (5H, m); 7.2 δ (2H, m); 4.08 δ (2H, s); 1.8 δ (5H, m); 1.4 δ (6H, m). ESI MS, Observed $(M+Na)^+=459$

Example 27

Compound 30

1-hydroxy-5-(2-naphthyl)-3-[(4-phenylphenyl)methyl] hydropyrazin-2-one is prepared by method A using Intermediate Compound 10 (110 mg) and 2-naphtylglyoxal (74 mg). Yield: 35%.

NMR: (300 MHz, DMSO-D6): 8.7 δ (1H, s); 8.42 δ (1H, s); 8.08 δ (1H, m); 7.96 δ (2H, m); 7.58 δ (4H, m); 7.4 δ (7H, m); 7.26 δ (1H, m); 4.2 δ (2H, s). ESI MS, Observed $(M+Na)^+=427$

Example 28

Compound 31

5-(4-bromophenyl)-1-hydroxy-3-[(4-phenylphenyl) methyl]hydropyrazin-2-one is prepared by method A using Intermediate Compound 10 (110 mg) and 4-bromophenylglyoxal (85 mg). Yield: 30%.

NMR: (300 MHz, DMSO-D6):8.6 δ (1H, s); 7.84 δ (2H, d); 7.6 δ (6H, m); 7.44 δ (4H, m); 7.3 δ (1H, m); 4.16 δ (2H, s). ESI MS, Observed (M+H)+=

Example 29

Compound 32

5-(2H-benzo[d]1,3-dioxolen-5-yl)-1-hydroxy-3-[(4-phenylphenyl)methyl] hydropyrazin-2-one is prepared by method A using Intermediate Compound 10 (110 mg) and 3,4-methylenedioxyphenylglyoxal (171 mg). Yield: 26%.

NMR: (300 MHz, DMSO-D6):8.62 δ (1H, s); 7.62 δ (4H, m); 7.42 δ (6H, m); 7.16 δ (1H, m); 6.94 δ (1H, d); 6.06 δ (2H, s); 4.08 δ (2H, s). ESI MS, Observed (M+Na)+=421

Example 30

Compound 33

4-{4-hydroxy-5-oxo-6-[(4-phenylphenyl)methyl]-4-hydropyrazin-2-yl} benzenecarbonitrile is prepared by method A using Intermediate Compound 10 (110 mg) and 4-cyanophenylglyoxal (64 mg). Yield: 35%.

NMR: (300 MHz, DMSO-D6): 8.76 δ (1H, s); 8.10 δ (2H, d); 7.82 δ (2H, d); 7.60 δ (4H, m); 7.40 δ (4H, m); 7.28 δ (1H, m); 4.18 δ (2H, s). ESI MS, Observed (M+Na)+=402

Intermediate Compound 34

2-(4-chloro-3 methylphenyl)-2-oxoethanal is prepared using a modified procedure from *J. Amer. Chem. Soc.* 88:865–866 (1966). 4-Chloro-3-methylphenacyl bromide 4-Chloro-3-methylphenacyl bromide (2.5 g 10 mmol) is dissolved in acetonitrile (25 mL). Silver nitrate (2.125 g 12.5 mmol) in acetonitrile (15 mL) is added with stirring to this solution. The mixture is stirred for 24 hours and silver bromide is filtered off and washed with acetonitrile, then the acetonitrile is rotovaped under vacuum. The residue is taken up in ether and washed with water and dried over anhydrous sodium sulphate and ether is rotovaped. The crude nitrate ester is dissolved in DMSO (50 mL) and added to a stirred solution of suspension of sodium acetate trihydrate (0.135 g) in DMSO (20 mL). After 30 minutes stirring at room temperature, the mixture is poured into 200 mL ice water, saturated with sodium chloride and extracted with ether. The ether extracts are washed with water and saturated sodium hydrogen carbonate solution, then dried over anhydrous sodium sulphate. Evaporation of the ether yields the glyoxal monohydrate derivative. The product is recrystallized from acetone/water. Yield 1.13 g (62%).

Intermediate Compound 35

2-(3,4-dichlorophenyl)-2-oxoethanal is prepared by a similar procedure to that used for the synthesis of Intermediate Compound 34, utilizing 3,4-Dichloropneacyl bromide 3,4-dichlorophenacylbromide (2.7 g) as the starting material. Yield: 2.0 g (98%).

Intermediate Compound 36

2-(4-methylphenyl)-2-oxoethanal is prepared by a similar procedure to that used for the synthesis of Intermediate Compound 34 utilizing 2-bromo-4'-methylacetophenone (2.1 g) as the starting material. Yield: 0.69 g (47%).

Intermediate Compound 37

2-(4-pentylphenyl)-2-oxoethanal is prepared by a similar procedure to that used for the synthesis of Intermediate Compound 34, utilizing 4-n pentylphenacylbromide (2.7 g) as the starting material. Yield: 1.79 g (88%).

Intermediate Compound 38

2-[4-(trifluoromethyl)phenyl]-2-oxoethanal is prepared by a similar procedure to that used for the synthesis of compound 34, utilizing 4-trifluoromethylphenacylbromide (2.7 g) as the starting material. Yield: 0.95 g (47%).

Example 31

Compound 39

5-(3,4-dichlorophenyl)-1-hydroxy-3-benzylhydropyrazin-2-one is prepared by method A using dl-phenylalanine hydroxamic acid (135 mg) and Intermediate Compound 35 (152 mg). Yield: 103 mg (40%).

NMR: (300 MHz, DMSO-D6): 8.70 δ (1H, s); 8.16 δ (1H, d); 7.90 δ (1H, m); 7.64 δ (1H, m); 7.30 δ (5H, m); 4.10 δ (2H, s).

Example 32

Compound 40

5-(4-chloro-3-methylphenyl)-1-hydroxy-3-benzylhydropyrazin-2-one is prepared by method A using dl-phenylalanine hydroxamic acid (135 mg) and Intermediate Compound 34 (137 mg). Yield: 100 mg (41%).

NMR: (300 MHz, DMSO-D6): 8.56 δ (1H, s); 7.92 δ (1H, m); 7.80 δ (1H, m); 7.40 δ (1H, m); 7.30 δ (4H, m); 7.20 δ (1H, m); 4.10 δ (2H, s); 2.30 δ (3H, s).

Example 33

Compound 41

1-hydroxy-5-(4-methylphenyl)-3-benzylhydropyrazin-2-one is prepared by method A using dl-phenylalanine hydroxamic acid (135 mg) and Intermediate Compound 36 (111 mg). Yield: 51 mg (23%).

NMR: (300 MHz, DMSO-D6): 8.46 δ (1H, s); 7.80 δ (2H, d); 7.26 δ (7H, m); 4.10 δ (2H, s); 2.24 δ (3H, s).

Example 34

Compound 42

1-hydroxy-5-(4-pentylphenyl)-3-benzylhydropyrazin-2-one is prepared by method A using dl-phenylalanine hydroxamic acid (135 mg) and Intermediate Compound 37 (153 mg). Yield: 71 mg (27%).

NMR: (300 MHz, DMSO-D6): 8.42 δ (1H, s); 7.80 δ (2H, d); 7.20 δ (7H, m); 4.10 δ (2H, s); 2.42 δ (2H, m); 1.60 δ (2H, t); 1.26 δ (4H, m); 0.82 δ (3H, t).

Example 35

Compound 43

1-hydroxy-3-benzyl-5-[4-(trifluoromethyl)phenyl] hydropyrazin-2-one is prepared by method A using dl-phenylalanine hydroxamic acid (135 mg) and Intermediate Compound 38 (152 mg). Yield: 158 mg (61%).

NMR: (300 MHz, DMSO-D6): 8.64 δ (1H, s); 8.20 δ (2H, d); 7.80 δ (2H, d); 7.40 δ (5H, m); 4.10 δ (2H, s).

Example 36

Compound 44

5-(3,4-dichlorophenyl)-1-hydroxy-3-[(4-phenylphenyl) methyl] hydropyrazin-2-one is prepared by method A using Intermediate Compound 10 (146 mg) and compound 35 (102 mg). Yield: 158 mg (61%).

NMR: (300 MHz, DMSO-D6): 8.70 δ (1H, s); 8.18 δ (1H, s); 7.86 δ (1H, m); 7.60 δ (5H, m); 7.40 δ (4H, m); 7.26 δ (1H, m); 4.16 δ (2H, s).

Example 37

Compound 45

5-(4-chloro-3-methylphenyl)-1-hydroxy-3-[(4-phenylphenyl)methyl] hydropyrazin-2-one is prepared by method A using Intermediate Compound 10 (146 mg) and Intermediate Compound 34 (192 mg). Yield: 158 mg (61%).

NMR: (300 MHz, DMSO-D6):8.58 δ (1H, s); 7.96 δ (1H, m); 7.76 δ (1H, m); 7.60 δ (4H, m); 7.38 δ (6H, m); 4.20 δ (2H, s); 2.20 δ (3H, s).

Example 38

Compound 46

1-hydroxy-5-(4-methylphenyl)-3-[(4-phenylphenyl)methyl]hydropyrazin-2-one is prepared by method A using Intermediate Compound 10 (146 mg) and Intermediate Compound 36 (74 mg). Yield: 158 mg (61%).

NMR: (300 MHz, DMSO-D6): 8.42 δ (1H, s); 7.80 δ (2H, d); 7.60 δ (4H, m); 7.40 δ (4H, m); 7.32 δ (1H, m); 7.20 δ (2H, d); 4.22 δ (2H, s); 2.24 δ (3H, s).

Example 39

Compound 47

1-hydroxy-5-(4-pentylphenyl)-3-[(4-phenylphenyl)methyl]hydropyrazin-2-one is prepared by method A using Intermediate Compound 10 (146 mg) and Intermediate Compound 37 (102 mg). Yield: 158 mg(61%).

NMR: (300 MHz, DMSO-D6): 8.42 δ (1H, s); 7.82 δ (1H, d); 7.60 δ (4H, m); 7.42 δ (4H, m); 7.30 δ (2H, m); 7.20 δ (2H, m); 4.18 δ (2H, s); 2.60 δ (2H, t); 1.60 δ (2H, t); 1.24 δ (4H, m); 0.82 δ (3H, t).

Example 40

Compound 48

1-hydroxy-3-[(4-phenylphenyl)methyl]-5-[4-(trifluoromethyl)phenyl] hydropyrazin-2-one is prepared by method A using Intermediate Compound 10 (146 mg) and Intermediate Compound 38 (101 mg). Yield: 158 mg (61%).

NMR: (300 MHz, DMSO-D6):8.68 δ (1H, s); 8.16 δ (2H, d); 7.78 δ (2H, d); 7.60 δ (4H, m); 7.40 δ (4H, m); 7.26 δ (1H, m); 4.22 δ (2H, s).

Example 41

The compounds of the present invention synthesized in Examples 1–40 are assayed in order to identify candidates with ALF inhibitory activity, generally according to the following protocols:

Gel Assay

ALF Cleavage Assay—Western Blot
Pre-incubation of Inhibitors with ALF:

7 μL of ALF (1 μg/mL) is pipetted into each vial, them 1 μL of DMSO or IpL of sample is added to the vials. The vials are vertexed and centrifuged for one minute. The vials are placed in a 30° C. water incubator for 30 minutes.

Addition of His Tagged Mek-1:

After 30 minutes, the samples are taken from the incubator, opened and 2 μL of His-tagged Mek-1 (0.5 μg/mL) is added to each of the vials. The vials are vertexed and centrifuged for one minute and transferred into 30° C. water incubator for 30 minutes.

Quenching the Assay:

After 30 minutes, the samples are taken from the incubator and 15 μL of SDS sample buffer (62.5 mM Tris-HCl, pH 6.8, 2% w/v SDS, 10% glycerol, 50 mM dithiothreitol (DTT), 0.1% w/v bromophenol blue) is added to each of the vials. The samples are vertexed and, if desired, stored at −20° C. prior to further analysis.

Western Blots:

SDS-polyacrylamide gel electrophoresis (SDS-PAGE) is performed on the samples by adding 44 μL of SDS sample buffer, boiling for 5 minutes, and running 30 μL aliquots on a 14% tris-glycine gel. The gel is then transferred onto nitrocellulose. The blot is rinsed twice with water, and the blocked with PBS containing 3% nonfat dry milk (PBS-MLK) for 20 minutes at room temperature.

The blot is then incubated with a 1:1000 dilution of α-Mouse MEK1-NT (or CT), diluted in PBS-MLK, overnight at 4° C. After incubation, the blot is washed twice with water, and incubated in anti-rabbit IgG linked to horseradish peroxidase, 1:2500 in PBS-MLK for 90 minutes at room temperature with agitation. The blot is again washed with water twice, then in PBS-00.5% Tween 20 for 3–5 minutes. The blot is rinsed in 4–5 changes of water, and enhanced chemiluminescence (ECL) is used to detect cleavage. Scion Image software is used to quantitate bands per lane and to quantitate control bands.

Plate Assay

Anthrax Lethal Factor Plate Assay Protocol

Materials:
ALF Protease: 1 mg/mL (20 μL/tube).
Substrate (GST-MEK1 fusion protein): 0.25 mg/mL (Upstate Biotechnology).
Reaction Buffer: 50 mM MOPS, pH 7.2.
Compounds in DMSO solution are diluted to 0.5 mM for screening.

III. Solution Reactions:
1). A Costar EIA/RIA plate (1/2 area flat bottom, 96-well) is blocked with 100 μL Superblock for 1 hour.
2). Master mixtures are added to each well of the plate, and 0.4 μL of test compound is added to each well. Substrates are added last. The wells are covered with parafilm and the plate is incubated at 37° C. for 16 hours.

Note: Reactions are carried out in 20 μL volume containing 0.2 μg GST-MEK1, 0.5 μg ALF in 50 mM MOPS buffer, pH 7.2 in the presence of 2.5 mg/mL BSA.

| Cpd | H$_2$O | 1 M buffer | 5% BSA | ALF | Substrate |
|---|---|---|---|---|---|
| 0.4 μL | 16.3 μL | 1 μL | 1 μL | 0.5 μL | 0.8 μL |

Negative controls are the reaction mixtures without addition of compounds; Positive controls are the reaction mixtures without additions of compounds and ALF.

IV. Plate Assay Protocol:
1). Coating. 100 μL 2 μg/mL rabbit anti-MEK1 (C-18) (Santa Cruz Biotech, carrier-free) are coated in 50 mM carbonate buffer, pH 8.1 in a 96-well plate, covered with parafilm and incubated at 4° C. for 16 hours.

2). Blocking. 200 μL SuperBlock is added, and incubated for 30 min.

3). Loading. Add 41 μL SuperBlock/Tween and 9 μL reaction mixture in each well. Incubate at RT for 1.5 hours.

4). Washing. 3 times in 200 μL TBST buffer.

5). Detection. 50 μL 0.5 μg/mL Eu-Anti GST antibody in SuperBlock/Tween are added, and incubated at RT for 1 hour.

6). Washing. 3 times in 200 μL TBST buffer.

7). Reading. Add 100 μL of Enhancement solution. Shake for 10 minutes and read Europium counts.

The results obtained from these assay protocols in determining the inhibitory activity of selected compounds of the present invention are presented in Table 1.

All patents and patent applications cited in this specification are hereby incorporated by reference as if they had been specifically and individually indicated to be incorporated by reference.

Although the foregoing invention has been described in some detail by way of illustration and Example for purposes of clarity and understanding, it will be apparent to those of ordinary skill in the art in light of the disclosure that certain changes and modifications may be made thereto without departing from the spirit or scope of the appended claims.

TABLE 1

Anthrax Lethal Factor Inhibitory Activity

| Chemical Name | Activity by Gel | Activity by plate |
|---|---|---|
| 1-hydroxy-3-(2-methylpropyl)-5,6-diphenylhydropyrazin-2-one | 0% @ 200 | |
| 5,6-diethyl-1-hydroxy-3-(2-methylpropyl)hydropyrazin-2-one | 0% @ 200 | |
| 1-hydroxy-6-methyl-3-(2-methylpropyl)-5-phenylhydropyrazin-2-one | 0% @ 200 | |
| 1-hydroxy-3-(2-methylpropyl)-5-phenylhydropyrazin-2-one | 0% @ 200 | |
| 1-hydroxy-5,6-diphenyl-3-benzylhydropyrazin-2-one | 45% @ 200 | IC 50 = 6 |
| 1-hydroxy-6-methyl-5-phenyl-3-benzylhydropyrazin-2-one | IC 50 = 43 | IC 50 = 70 |
| 1-hydroxy-5-phenyl-3-benzylhydropyrazin-2-one | IC 50 = 22 | IC 50 = 15 |
| 1-hydroxy-5,6-diphenyl-3-[(4-phenylphenyl)methyl]hydropyrazin-2-one | 2% @ 100 | |
| 1-hydroxy-6-methyl-5-phenyl-3-[(4-phenylphenyl)methyl]hydropyrazin-2-one | IC 50 = 3.6 | IC 50 = 15 |
| 1-hydroxy-5-phenyl-3-[(4-phenylphenyl)methyl]hydropyrazin-2-one | IC 50 = 2.6 | |
| 1-hydroxy-5-(4-morpholin-4-ylphenyl)-3-benzylhydropyrazin-2-one | | 0% @ 100 |
| 5-(4-fluorophenyl)-1-hydroxy-3-benzylhydropyrazin-2-one | | 33% @ 100 |
| 1-hydroxy-3-benzyl-5-(2-thienyl)hydropyrazin-2-one | | 33% @ 100 |
| 1-hydroxy-3-benzyl-5-(4-phenylphenyl)hydropyrazin-2-one | | 41% @ 100 |
| 5-(4-cyclohexylphenyl)-1-hydroxy-3-benzylhydropyrazin-2-one | | IC 50 = 8 |
| 1-hydroxy-5-(2-naphthyl)-3-benzylhydropyrazin-2-one | | 59% @ 100 |
| 5-(4-bromophenyl)-1-hydroxy-3-benzylhydropyrazin-2-one | | 63% @ 100 |
| 1-hydroxy-5-(4-hydroxyphenyl)-3-benzylhydropyrazin-2-one | | 7% @ 100 |
| 5-(2H-benzo[d]1,3-dioxolen-5-yl)-1-hydroxy-3-benzylhydropyrazin-2-one | | 39% @ 100 |
| 1-hydroxy-5-(4-nitrophenyl)-3-benzylhydropyrazin-2-one | | 7% @ 100 |
| 4-[4-hydroxy-5-oxo-6-benzyl-4-hydropyrazin-2-yl]-benzenecarbonitrile | | 41% @ 100 |
| N-{4-[4-hydroxy-5-oxo-6-benzyl-4-hydropyrazin-2-yl]-phenyl}acetamide | | 19% @ 100 |
| 1-hydroxy-5-(4-morpholin-4-ylphenyl)-3-[(4-phenylphenyl)methyl]hydropyrazin-2-one | | 37% @ 100 |
| 5-(4-fluorophenyl)-1-hydroxy-3-[(4-phenylphenyl)methyl]hydropyrazin-2-one | | 12% @ 100 |
| 1-hydroxy-5-(4-phenylphenyl)-3-[(4-phenylphenyl)methyl]hydropyrazin-2-one | | IC 50 = 12 |
| 5-(4-cyclohexylphenyl)-1-hydroxy-3-[(4-phenylphenyl)methyl]hydropyrazin-2-one | | 59% @ 100 |
| 1-hydroxy-5-(2-naphthyl)-3-[(4-phenylphenyl)methyl]hydropyrazin-2-one | | 54% @ 100 |
| 5-(4-bromophenyl)-1-hydroxy-3-[(4-phenylphenyl)methyl]hydropyrazin-2-one | | IC 50 = 5 |
| 5-(2H-benzo[d]1,3-dioxolen-5-yl)-1-hydroxy-3-[(4-phenylphenyl)methyl]hydropyrazin-2-one | | 40% @ 100 |
| 4-{4-hydroxy-5-oxo-6-[(4-phenylphenyl)methyl]-4-hydropyrazin-2-yl}-benzenecarbonitrile | | 51% @ 100 |
| 5-(3,4-dichlorophenyl)-1-hydroxy-3-benzylhydropyrazin-2-one | | 45% @ 100 |
| 5-(4-chloro-3-methylphenyl)-1-hydroxy-3-benzylhydropyrazin-2-one | | 18% @ 100 |
| 1-hydroxy-5-(4-methylphenyl)-3-benzylhydropyrazin-2-one | | 13% @ 100 |
| 1-hydroxy-5-(4-pentylphenyl)-3-benzylhydropyrazin-2-one | | 16% @ 100 |
| 1-hydroxy-3-benzyl-5-[4-(trifluoromethyl)phenyl]hydropyrazin-2-one | | 0% @ 100 |
| 5-(3,4-dichlorophenyl)-1-hydroxy-3-[(4-phenylphenyl)methyl]hydropyrazin-2-one | | 45% @ 100 |
| 5-(4-chloro-3-methylphenyl)-1-hydroxy-3-[(4-phenylphenyl)methyl]hydropyrazin-2-one | | 47% @ 100 |
| 1-hydroxy-5-(4-methylphenyl)-3-[(4-phenylphenyl)methyl]hydropyrazin-2-one | | 46% @ 100 |
| 1-hydroxy-5-(4-pentylphenyl)-3-[(4-phenylphenyl)methyl]hydropyrazin-2-one | | 39% @ 100 |
| 1-hydroxy-3-[(4-phenylphenyl)methyl]-5-[4-(trifluoromethyl)phenyl]hydropyrazin-2-one | | 25% @ 100 |

What is claimed is:

1. A method for preventing or treating anthrax infections by inhibiting anthrax lethal factor activity comprising administering a compound of the formula:

$$\begin{array}{c} \text{OH} \\ R1 \diagdown \underset{|}{N} \diagup O \\ R2 \diagdown \underset{N}{\diagdown} \diagup R4 \\ R3 \end{array}$$

Wherein

R1, R2, R3 and R4 are each independently selected from H, hydroxyl, alkoxy, alkylthio, small alkyl (C1–C10) (unsubstituted or substituted with alkyl, cycloalkyl fluoro, aryl, heteroaryl, alkylthio, arylthio, cyano, OR6, OC=OR6, C=O—OR7, or C=O—NR8R9), phenyl and mono and disubstituted (at positions 3 and 4) phenyl (wherein the phenyl ring is independently substituted with alkyl, trifluoromethyl, mono and di halogen atoms, alkylthio, alkoxy, nitro, cyano, morphilino, cyclohexyl, phenyl, phenolic, dioxymethylene, nitro, acetylamino);

heteroaryl (unsubstituted or substituted with alkyl, halogen, alkylthio, alkoxy, or nitro), cycloalkyl (C3–C10) (unsubstituted or substituted with alkyl, fluoro, aryl, heteroaryl, alkylthio, arylthio, cyano, OR5, OC=OR5, C=O—OR6, or C=O—NR7R8)

alkenyl (C1–C10) (unsubstituted or substituted with alkyl, fluoro, aryl, heteroaryl, alkylthio, arylthio, cyano, OR5, OC=OR5, C=O—OR6, or C=O—NR7R8)

alkadienyl (C1–C10) (unsubstituted or substituted with alkyl, fluoro, aryl, heteroaryl, alkylthio, arylthio, cyano, OR5, —OC=OR5, —C=O—OR6, C=O—NR7R8)

cycloalkenyl (C4–C10), unsubstituted or substituted with alkyl, fluoro, aryl, heteroaryl, alkylthio, arylthio, cyano, OR5, —OC=OR5, —C=O—OR6, C=O—NR7R8 bicycloalkyl (C5–C12), unsubstituted or substituted with alkyl, fluoro, aryl, heteroaryl, alkylthio, arylthio, cyano, OR5, —OC=OR5, —C=O—OR6, C=O—NR7R8 tricycloalkyl (C8–C14), unsubstituted or substituted with alkyl, fluoro, aryl, heteroaryl, alkylthio, arylthio, cyano, OR5, —OC=OR5, —C=O—OR6, C=O—NR7R8 where

R5 is alkyl (C1–C10), unsubstituted or substituted with alkyl, keto, fluoro, alkoxy, alkylthio, aryl, heteroaryl, cyano, aryloxy, cycloalkyl;

aryl, unsubstituted or substituted with alkyl, keto, fluoro, alkoxy, alkylthio, cyano, aryloxy;

heteroaryl, unsubstituted or substituted with alkyl, keto, fluoro, alkoxy, alkylthio, cyano, aryloxy;

cycloalkyl, unsubstituted or substituted with alkyl, keto, fluoro, alkoxy, alkylthio, aryl, heteroaryl, cyano:

R6 is alkyl (C1–C10), unsubstituted or substituted with alkyl, keto, fluoro, alkoxy, alkylthio, aryl, heteroaryl;

aryl, unsubstituted or substituted with alkyl, keto, fluoro, alkoxy, alkylthio;

heteroaryl, unsubstituted or substituted with alkyl, keto, fluoro, alkoxy, alkylthio;

cycloalkyl, unsubstituted or substituted with alkyl, keto, fluoro, alkoxy, alkylthio, aryl, heteroaryl;

R7 is alkyl (C1–C10), unsubstituted or substituted with alkyl, keto, fluoro, alkoxy, alkylthio, aryl, heteroaryl;

aryl, unsubstituted or substituted with alkyl, keto, fluoro, alkoxy, alkylthio;

heteroaryl, unsubstituted or substituted with alkyl, keto, fluoro, alkoxy, alkylthio;

cycloalkyl, unsubstituted or substituted with alkyl, keto, fluoro, alkoxy, alkylthio, aryl, heteroaryl; and R8 is alkyl (C1–C10), unsubstituted or substituted with alkyl, keto, fluoro, alkoxy, alkylthio, aryl, heteroaryl;

aryl, unsubstituted or substituted with alkyl, keto, fluoro, alkoxy, alkylthio;

heteroaryl, unsubstituted or substituted with alkyl, keto, fluoro, alkoxy, alkylthio;

cycloalkyl, unsubstituted or substituted with alkyl, keto, fluoro, alkoxy, alkylthio, aryl, heteroaryl, together with a pharmaceutically acceptable carrier to a patient in need of such treatment.

2. A method as recited in claim 1 for preventing or treating anthrax infections by inhibiting anthrax lethal factor activity comprising administering a compound of the formula:

$$\begin{array}{c} \text{OH} \\ R1 \diagdown \underset{|}{N} \diagup O \\ R2 \diagdown \underset{N}{\diagdown} \diagup R4 \\ R3 \end{array}$$

Wherein

R1 is selected from H, small alkyl ($C_{1-6}$), hydroxyl, alkoxy, thioalkyl, phenyl and mono and disubstituted (at positions 3 and 4) phenyl (wherein the phenyl ring is independently substituted with alkyl, trifluoromethyl, mono and di halogen atoms, cyano, morphilino, cyclohexyl, phenyl, phenolic, dioxymethylene, nitro, acetylamino);

R2 is selected from small alkyl ($C_{1-6}$), phenyl, mono and disubstituted (at positions 3 and 4) phenyl (wherein the phenyl ring is independently substituted with alkyl, trifluoromethyl, mono and di halogen atoms, cyano, morphilino, cyclohexyl, phenyl, phenolic, dioxymethylene, nitro, acetylamino), thiophenyl, and naphthyl groups;

R3 is H, small alkyl ($C_{1-6}$), hydroxyl, alkoxy, thioalkyl, phenyl and mono and disubstituted (at positions 3 and 4) phenyl (wherein the phenyl ring is independently substituted with alkyl, trifluoromethyl, mono and di halogen atoms, cyano, morphilino, cyclohexyl, phenyl, phenolic, dioxymethylene, nitro, acetylamino); and R4 is H, together with a pharmaceutically acceptable carrier to a patient in need of such treatment.

3. A method as recited in claim 1 wherein the compound is at least one member selected from the group consisting of 1-hydroxy-3-(2-methylpropyl)-5,6-diphenylhydropyrazin-2-one
5,6-diethyl-1-hydroxy-3-(2-methylpropyl)hydropyrazin-2-one
1-hydroxy-6-methyl-3-(2-methylpropyl)-5-phenylhydropyrazin-2-one
1-hydroxy-3-(2-methylpropyl)-5-phenylhydropyrazin-2-one
1-hydroxy-5,6-diphenyl-3-benzylhydropyrazin-2-one
1-hydroxy-6-methyl-5-phenyl-3-benzylhydropyrazin-2-one
1-hydroxy-5-phenyl-3-benzylhydropyrazin-2-one
1-hydroxy-5,6-diphenyl-3-[(4-phenylphenyl)methyl]hydropyrazin-2-one
1-hydroxy-6-methyl-5-phenyl-3-[(4-phenylphenyl)methyl]hydropyrazin-2-one
1-hydroxy-5-phenyl-3-[(4-phenylphenyl)methyl]hydropyrazin-2-one
1-hydroxy-5-(4-morpholin-4-ylphenyl)-3-benzylhydropyrazin-2-one
5-(4-fluorophenyl)-1-hydroxy-3-benzylhydropyrazin-2-one
1-hydroxy-3-benzyl-5-(2-thienyl)hydropyrazin-2-one
1-hydroxy-3-benzyl-5-(4-phenylphenyl)hydropyrazin-2-one
5-(4-cyclohexylphenyl)-1-hydroxy-3-benzylhydropyrazin-2-one
1-hydroxy-5-(2-naphthyl)-3-benzylhydropyrazin-2-one
5-(4-bromophenyl)-1-hydroxy-3-benzylhydropyrazin-2-one
1-hydroxy-5-(4-hydroxyphenyl)-3-benzylhydropyrazin-2-one
5-(2H-benzo[d]1,3-dioxolen-5-yl)-1-hydroxy-3-benzylhydropyrazin-2-one
1-hydroxy-5-(4-nitrophenyl)-3-benzylhydropyrazin-2-one
4-[4-hydroxy-5-oxo-6-benzyl-4-hydropyrazin-2-yl]benzenecarbonitrile
N-{4-[4-hydroxy-5-oxo-6-benzyl-4-hydropyrazin-2-yl]phenyl}acetamide
1-hydroxy-5-(4-morpholin-4-ylphenyl)-3-[(4-phenylphenyl)methyl]hydropyrazin-2-one
5-(4-fluorophenyl)-1-hydroxy-3-[(4-phenylphenyl)methyl]hydropyrazin-2-one
1-hydroxy-5-(4-phenylphenyl)-3-[(4-phenylphenyl)methyl]hydropyrazin-2-one
5-(4-cyclohexylphenyl)-1-hydroxy-3-[(4-phenylphenyl)methyl]hydropyrazin-2-one
1-hydroxy-5-(2-naphthyl)-3-[(4-phenylphenyl)methyl]hydropyrazin-2-one
5-(4-bromophenyl)-1-hydroxy-3-[(4-phenylphenyl)methyl]hydropyrazin-2-one
5-(2H-benzo[d]1,3-dioxolen-5-yl)-1-hydroxy-3-[(4-phenylphenyl)methyl]hydropyrazin-2-one
4-{4-hydroxy-5-oxo-6-[(4-phenylphenyl)methyl]-4-hydropyrazin-2-yl}benzenecarbonitrile
5-(3,4-dichlorophenyl)-1-hydroxy-3-benzylhydropyrazin-2-one
5-(4-chloro-3-methylphenyl)-1-hydroxy-3-benzylhydropyrazin-2-one
1-hydroxy-5-(4-methylphenyl)-3-benzylhydropyrazin-2-one
1-hydroxy-5-(4-pentylphenyl)-3-benzylhydropyrazin-2-one
1-hydroxy-3-benzyl-5-[4-(trifluoromethyl)phenyl]hydropyrazin-2-one
5-(3,4-dichlorophenyl)-1-hydroxy-3-[(4-phenylphenyl)methyl]hydropyrazin-2-one
5-(4-chloro-3-methylphenyl)-1-hydroxy-3-[(4-phenylphenyl)methyl]hydropyrazin-2-one
1-hydroxy-5-(4-methylphenyl)-3-[(4-phenylphenyl)methyl]hydropyrazin-2-one
1-hydroxy-5-(4-pentylphenyl)-3-[(4-phenylphenyl)methyl]hydropyrazin-2-one
1-hydroxy-3-[(4-phenylphenyl)methyl]-5-[4-(trifluoromethyl)phenyl]hydropyrazin-2-one.

* * * * *